US006248350B1

(12) United States Patent
Mori et al.

(10) Patent No.: US 6,248,350 B1
(45) Date of Patent: Jun. 19, 2001

(54) EXTERNAL FORMULATION CONTAINING LOXOPROFEN

(75) Inventors: Masao Mori; Hidetsune Tamaoki, both of Toyama; Tamaki Horiuchi, Oyaba, all of (JP)

(73) Assignee: Lead Chemical Co., Ltd., Toyama-ken (JP)

(*) Notice: Subject to any disclaimer, the term of this patent is extended or adjusted under 35 U.S.C. 154(b) by 0 days.

(21) Appl. No.: 09/242,555

(22) PCT Filed: Aug. 25, 1997

(86) PCT No.: PCT/JP97/02936

§ 371 Date: Feb. 19, 1999

§ 102(e) Date: Feb. 19, 1999

(87) PCT Pub. No.: WO98/08966

PCT Pub. Date: Mar. 5, 1998

(30) Foreign Application Priority Data

Aug. 26, 1996 (JP) .................................................... 8-223524

(51) Int. Cl.$^7$ ............................ A61K 9/70; A61K 31/04; A61K 31/015; A61F 13/02
(52) U.S. Cl. ........................... 424/449; 424/447; 424/448; 514/764; 514/741
(58) Field of Search ...................................... 435/190, 132, 435/135; 514/510, 741, 764; 424/449, 447, 448

(56) References Cited

U.S. PATENT DOCUMENTS 5,322,685 * 6/1994 Nakagawa et al. .
5,352,437 * 10/1994 Nakagawa et al. .
5,446,070 * 8/1995 Mantelle .

FOREIGN PATENT DOCUMENTS

| 57-4919 | 1/1982 | (JP) . |
| 62-126119 | 6/1987 | (JP) . |
| 62-181226 | 8/1987 | (JP) . |
| 3-72433 | 3/1991 | (JP) . |
| 4-99719 | 3/1992 | (JP) . |
| 4-275235 | 9/1992 | (JP) . |
| 4-321624 | 11/1992 | (JP) . |
| 8-165251 | 6/1996 | (JP) . |
| 8-295624 | 11/1996 | (JP) . |

OTHER PUBLICATIONS

Hay et al., Journal of Endocrinology, vol. 79, No. 1, pp. 29–39, 1978.*
Tanaka et al., Japanese Journal of Inflammation vol. 3, No. 2, Spring, 1983, pp. 15–155.
Tanaka, Yorihisa et al., "Purification and Some Properties of Ketone Reductase Forming an Active Metabolite Sodium 2–[4–(2–Oxocyclopentylmethyl)phenyl]propionate Dihydrate (Loxoprofen Sodium), a New Anti–inflammatory Agent, in Rabbit Liver Cytosol,," Chemical & Pharmaceutical Bulletin, vol. 32, No. 3, 1984, pp. 1040–1048.
Naganuma, Hideo et al., "Stereospecificity of Enzymatic Hydrogen Transfer to Loxoprofen, A Non–Steroidal Anti–inflammatory Agent, in the Rat," Research Communication in Chemical Pathology and Pharmacology, vol. 69, No. 2, 1990, pp. 173–185.
Tanaka, Yorihisa, "Stereoselective Metabolism Studies on Loxoprofen, a 2–Arylpropionic Acid Nonsteroidal Anti–inflammatory Drug, and Its Role for the Development as Prodrug," Yakubutsu Dotai, vol. 8, No. 5, 1993, pp. 521–536.
Takasaki, Wataru, "Application of Antibody–Medicated Extraction for the Stereoselective Determination of the Active Metabolite of Loxoprofen in Human and Rat Plasma," Chirality, vol. 5, N.o. 5, pp. 308–315, 1992.
Nagashima, Hisomu, "Column Liquid Chromatography for the Simultaneous Determination of the Enantiomers of Loxoprofen Sodium and Its Metabolites in Human Urine," Journal of Chromatography, vol. 345, No. 2, 1985, pp. 373–379.
Matsuda et al., Japanese Journal of Inflammation, vol. 2, No. 3, Summer, pp. 263–266 (1982).

* cited by examiner

Primary Examiner—Francisco Prats
Assistant Examiner—Susan D. Coe
(74) Attorney, Agent, or Firm—Oliff & Berridge, PLC

(57) ABSTRACT

An anti-inflammatory analgesic patch containing loxoprofen, crotamiton, solvent, skin permeation accelerator, water-soluble polymers and moisturizers. The patch allows for the loxoprofen to penetrate the skin.

3 Claims, No Drawings

EXTERNAL FORMULATION CONTAINING LOXOPROFEN

TECHNICAL FIELD

The present invention relates to an anti-inflammatory analgesic external formulation containing Loxoprofen or its pharmaceutically acceptable salt as an active ingredient.

BACKGROUND ART

A sodium salt of Loxoprofen (formal name: 2-[p-(2-oxocyclopentylmethyl)phenyl] propionic acid), otherwise known as Loxoprofen sodium, has excellent efficacy as a phenylpropionic acid type nonsteroidal anti-inflammatory agent and is widely used as a medicine for internal use under the trade name of "Loxonin."

By the way, Loxoprofen sodium is a prodrug. When orally administered, it is metabolized in the body into a trans-OH form (formal name: 2-[p-(trans-2-hydroxycyclopentyl-methyl)phenyl] propionic acid), which exhibits excellent anti-inflammatory activities, as is known in the art [Matsuda et al. Japanese Journal of Inflammation, Vol. 2, No. 3, Summer, pp. 263 to 266 (1983)]. An enzyme (a ketone-reducing enzyme) which is associated with this metabolism, mainly exists in the liver and kidney [Tanaka et al., Japanese Journal of Inflammation, Vol. 3, No. 2, Spring, pp. 151 to 155 (1983)], and the trans-OH form is known to exhibit inhibitory activity against cyclooxygenase, a prostaglandin producing enzyme, approximately 80 times as potently as Loxoprofen sodium [Matsuda et al. Japanese Journal of Inflammation, Vol. 2, No. 3, Summer, pp.263 to 266 (1983)]. Accordingly, it has been understood that Loxoprofen sodium must pass through the liver or kidney, where it is activated, before Loxoprofen sodium can exhibit its excellent anti-inflammatory analgesic activities.

Thus, when Loxoprofen sodium is used as an external formulation, it should not be treated in the same manner as anti-inflammatory analgesics, such as indomethacin, ibuprofen and ketoprofen, in case of which the drug itself provides a pharmacological effect.

However, hitherto, many patent applications have been filed for external formulations containing an anti-inflammatory analgesic as an active ingredient, in particular, for bases for external formulations, and some of them cite an anti-inflammatory analgesic as an example of an active ingredient that is contained in the formulation or that can be added to the base, and further, some of them cite Loxoprofen sodium as a specific example of the anti-inflammatory analgesic. Most of these applications, however, simply cite Loxoprofen as a mere example of the anti-inflammatory analgesic in the specification. Although some of these patent applications refer to crotamiton as an example of a solvent for active ingredients, which is one of the constituent features of the present application, none of the applications, in fact, does specifically disclose a formulation containing Loxoprofen and crotamiton.

On the other hand, in respect to Loxoprofen and its sodium salt, the external formulation are disclosed concretely in (1) Japanese Patent Application Laid Open No. Hei 4-99719, (2) Japanese Patent Application Laid Open No. Hei 8-165251, and (3) Japanese Patent Application Laid Open No. Sho 57-4919.

(1) is an invention on a novel base containing a certain type of fatty acid ester and polyhydric alcohols and intends to increase the speed at which an active ingredient permeates through the skin and a transdermal patch the base of which contains Loxoprofen sodium is prepared as an example there.

(2) discloses a specific solvent, [2-(2-methoxy-1-methylethyl)-5-methylcyclohexanol] and, an external formulation containing said solvent, a patch containing Loxoprofen is prepared as an example there, and its tackiness and safety to the skin are evaluated in the test examples. However, none of the patent applications refer to pharmacological effects of Loxoprofen sodium in the case where it is administered in the form of an external formulation.

In addition, when the present inventors prepared an external formulation of Loxoprofen sodium containing a fatty acid ester and a polyhydric alcohol in accordance with (1) and observed it with the passage of time, crystals of Loxoprofen were deposited. In general, when an external formulation of a certain compound is prepared, a solvent is added in order to avoid the crystallization and deposition of the active ingredient. The selection of an optimal solvent is an important element for the design of a formulation. Depending on the type of a selected solvent, there may occur a decreased release of the active ingredient from the base and a decreased transfer of it to the affected part because of the insufficient dissolution of the drug, thereby failing to provide sufficient therapeutical effects. In other words, a solvent that is optimal for a particular active ingredient cannot be expected to be also optimal for other active ingredients.

On the other hand, Japanese Patent Application Laid Open No. Sho 57-4919 (the above mentioned (3)) describes, in test examples, the pharmacological effects as external formulations of a solution of Loxoprofen in croton oil and of an ointment obtained by simply adding Loxoprofen sodium to Plastibase 50W. Croton oil, however, is a toxic substance which is used as an irritant and cocarcinogen in the research of cancer [THE MERCK INDEX, twelfth edition, pp. 2665] so that it is inappropriate to mix such a substance into a medicine. In addition, the efficacy of a formulation comprising a combination of Loxoprofen sodium and Plastibase 50W does not exhibit dosage dependence.

DISCLOSURE OF THE INVENTION

Problems to Be Solved by the Invention

As described above, Loxoprofen is a prodrug, it is its trans-OH form, an active metabolite, that exhibits strong anti-inflammatory analgesic activities, and the enzyme that serves to convert Loxoprofen into an active metabolite mostly exists in the liver and kidney. Hence, the present inventors supposed that for topical administration, the transcutaneous absorption of trans-OH form of Loxoprofen allows the trans-OH form to be maintained at its applied site in a larger amount to achieve an excellent anti-inflammatory analgesic activities than the transcutaneous absorption of Loxoprofen. However, tests by the present inventors on the trans-OH form for its transcutaneous absorption revealed that the trans-OH form could very hardly be absorbed.

As a result of the intensive research on anti-inflammatory analgesic external formulation containing Loxoprofen sodium as an active ingredient, the present inventors have found that (i) Loxoprofen as such has a superior permeability through the skin to the trans-OH form, which is an active metabolite, so that transcutaneous administration enables a sufficient amount of Loxoprofen to be accumulated in the skin, and that (ii) if a sufficient amount of Loxoprofen is retained in the skin over a long period of time, it is surprisingly transformed by the ketone- reducing enzyme into the trans-OH form even in the skin and an effective amount of trans-OH form can be maintained therein. With respect to the above problem of the formulation of Loxoprofen, the present inventors have found that the use of crotamiton as a solvent prevents Loxoprofen from being deposited in the form of crystal, thereby providing an external formulation of Loxoprofen that has high stability and that shows no skin irritation. That is, mixing crotamiton as a solvent into an external formulation of Loxoprofen prevents Loxoprofen from being deposited as crystals, and as a result a formulation is obtained which has excellent uniformity in the distribution of the active ingredient. This formulation enables a substantial increase in the rate and amount of transcutaneous absorption of Loxoprofen and also a continuous supply of Loxoprofen, thereby allowing a sufficient concentration of Loxoprofen to be persistently maintained in the skin at the applied site. Then, as confirmed first by the present inventors, Loxoprofen is converted into the trans-OH form in the skin so as to allow a sufficient amount of trans-OH form to be maintained at the applied site. As a result, it has been found that application of this formulation provides an excellent topical anti-inflammatory analgesic effect and that the formulation shows no skin irritation. Based on these findings, the present inventors have completed the present invention.

(Means for Solving the Problems)

The present invention relates to:

(1) a method for producing a trans-OH form comprising converting Loxoprofen or its pharmaceutically acceptable salt into a trans-OH form thereof with a ketone-reducing enzyme existing in the skin; and (2) an anti-inflammatory analgesic external formulation containing Loxoprofen or its pharmaceutically acceptable salt and crotamiton.

The anti-inflammatory analgesic external formulation described in (2) is preferably an external formulation characterized in that:

(3) application of the external formulation causes Loxoprofen or its pharmaceutically acceptable salt to be metabolized into a trans-OH form thereof in the skin and wherein the trans-OH form is higher in concentration in a dermal layer of the skin at an applied site than in blood plasma.

Of the anti-inflammatory analgesic external formulation described in (2) or (3), more preferred is:

(4) an external formulation wherein the content of crotamiton is 0.5 to 5% by weight of the total weight of the formulation;

(5) an external formulation wherein the content of crotamiton is 1 to 2% by weight of the total weight of the formulation;

(6) an external formulation wherein the content of Loxoprofen or its pharmaceutically acceptable salt is 0.1 to 5% by weight of the total weight of the formulation;

(7) an external formulation wherein the content of Loxoprofen or its pharmaceutically acceptable salt is 0.15 to 2% by weight of the total weight of the formulation; or (8) an external formulation wherein the content of Loxoprofen or its pharmaceutically acceptable salt is 0.5 to 2% by weight of the total weight of the formulation.

Another preferred anti-inflammatory analgesic external formulation is an arbitrary combination of elements each selected from the groups consisting of (2) and (3), (4) and (5), and (6) to (8).

In addition to Loxoprofen or its pharmaceutically acceptable salt and crotamiton, the anti-inflammatory analgesic external formulation mentioned above can include an additives commonly used in external formulations. Preferred examples of such anti-inflammatory analgesic external formulations include in addition to Loxoprofen or its pharmaceutically acceptable salt and crotamiton:

(9) an external formulation containing 0.5 to 80% by weight of a solvent and/or a skin permeation accelerator of the total weight of the formulation;

(10) an external formulation containing 3 to 30% by weight of the formulation of a water-soluble polymer of the total weight;

(11) an external formulation containing 5 to 20% by weight of a water-soluble polymer of the total weight of the formulation;

(12) an external formulation containing 5 to 95% by weight of an oil-soluble polymer of the total weight of the formulation;

(13) an external formulation containing 10 to 80% by weight of an oil-soluble polymer of the total weight of the formulation;

(14) an external formulation containing 5 to 60% by weight of a moisturizer of the total weight of the formulation; or

(15) an external formulation containing 10 to 45% by weight of a moisturizer of the total weight of the formulation.

Further, formulations which include two or more elements selected from (10) to (15) are also preferred. [However, (10) and (11) cannot be selected simultaneously and (14) and (15) cannot be selected simultaneously.]

Furthermore, it is another object of this invention to provide an anti-inflammatory analgesic external formulation described in any one selected from (2) to (15) above, in the form of a patch, an ointment, a cream, a lotion, or an aerosol.

According to this invention, the term "pharmaceutically acceptable salt" in the definition of "Loxoprofen or its pharmaceutically acceptable salt" refers to a salt of a cation with a carboxyl group that is contained in the molecule of Loxoprofen. Such salts preferably include alkali metal salts such as sodium salt, potassium salt, and lithium salt; alkaline earth metal salts such as calcium salt and magnesium salt; metal salts such as aluminum salt, iron salt, zinc salt, copper salt, nickel salt, and cobalt salt; ammonium salts; amine salts such as t-octylamine salt, dibenzylamine salt, morpholine salt, glucosamine salt, salt of an alkyl ester of phenylglycine, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl) aminomethane salt, and other such organic salts; and amino acid salts such as glycine salt, lysine salt, arginine salt, ornithine salt, glutamic acid salt, and aspartic acid salt. The pharmaceutically acceptable salt is more preferably a water-soluble salt and most preferably a sodium salt.

Moreover, when left in the air or recrystallized, the "Loxoprofen or its pharmaceutically acceptable salt" absorbs water or the solvent used for recrystallization to become a hydrate or solvate, which is also included in this invention.

Whether a certain external formulation is a formulation wherein "application of the external formulation causes Loxoprofen or its pharmaceutically acceptable salt to be metabolized into a trans-OH form thereof in the skin and wherein the concentration of trans-OH form is higher in a dermal layer of the skin at an applied site than in blood plasma" can be checked by applying the external formulation to, for example, test animals such as rats or mice and measuring the concentrations of trans-OH form (μg/ml) in the blood plasma and in the dermal layer of the skin at the applied site at a certain time (for example, four or eight hours) after the application. Specifically, this can be easily checked by conducting experiments according to the method described in "Test Example 3" described later.

With respect to this invention, the content of Loxoprofen sodium in the external formulation is not limited to any particular range as long as formulation is feasible, but is preferably between 0.1% by weight (more preferably 0.15% by weight and most preferably 0.5% by weight) and 5% by weight (more preferably 2% by weight) of the total weight of the formulation. An excessively small amount of active ingredient provides insufficient efficacy, while an excessively large amount of active ingredient provides no advantages and is thus not cost-effective.

The content of crotamiton used as a solvent is not particularly limited as long as formulation is feasible, but is preferably between 0.5% by weight (more preferably 1% by weight) and 5% by weight (more preferably 2% by weight) of the total weight of the formulation.

The pH of the external formulation is preferably between 4.0 (more preferably 5.0 and most preferably 5.5) and 7.5 (more preferably 7.0 and most preferably 6.5).

The present external formulation may include various bases used for common external formulations, for example, another solvent that can be used with crotamiton; a skin permeation accelerator, a water-soluble polymer that can be used as an adhesive agent and/or a film-former; an oil-soluble polymeric compound that can be used as an adhesive agent and/or a tackifier; a moisturizer; a surfactant; a propellant; and other pharmaceutically acceptable additives, without limitation, unless they do not have adverse effects.

Other solvents that dissolve Loxoprofen or its pharmaceutically acceptable salt is not particularly limited as long as it can be used with crotamiton without providing adverse effects, and is selected from, for example, water, alcohols, pharmaceutically acceptable fatty acids and their esters, and oily components such as animal oils, vegetable oils, and terpene compounds.

If water is used, its content is preferably between 20% by weight (more preferably 40% by weight) and 80% by weight (more preferably 60% by weight) of the total weight of the formulation.

The alcohols may be any common alcohol without particular limitation as long as it has no adverse effect. Such an alcohol includes, for example, aliphatic alcohols such as methanol, ethanol, propyl alcohol, and isopropyl alcohol; aliphatic polyhydric alcohols such as propylene glycol, octanediol, 1,3-butanediol, ethylene glycol, polyethylene glycol, glycerol, and D-sorbitol; and aromatic aliphatic alcohols such as benzyl alcohol. The content of such an alcohol is preferably between 0.5% by weight (more preferably 3% by weight) and 10% by weight (more preferably 5% by weight) of the total weight of the formulation. However, the content of propylene glycol, polyethylene glycol, glycerol, or D-sorbitol used as the moisturizer described later is not limited to these values.

The pharmaceutically acceptable fatty acid and its ester may be any common fatty acid and ester without particular limitation as long as they have no adverse effect. The pharmaceutically acceptable fatty acid and ester thereof is preferably a fatty acid that has 3 (more preferably 10) to 30 (more preferably 20) carbon atoms, for example, capric acid, lauric acid, myristic acid, palmitic acid, oleic acid, linolic acid, stearic acid, lauryl lactate, isopropyl myristate, isopropyl palmitate, oleyl oleate, diisopropyl adipate, diisopropyl sebacate, glycerol monocaprylate, or ethylene glycol monoisooctanoate. Its ester is preferably an alkyl ester having 5 (more preferably 12) to 50 (more preferably 40) carbon atoms or an alkylene glycol ester having 8 (more preferably 12) to 30 (more preferably 24) carbon atoms. One or more fatty acids and their esters may be used in combination. A preferred fatty acid is oleic acid or lauryl lactate. The content of such an fatty acid or its ester is preferably between 0.5% by weight (more preferably 1% by weight) and 20% by weight (more preferably 15% by weight) of the total weight of the formulation.

The oily component such as animal oil, vegetable oil, and a terpene compound maybe any common oily component without particular limitation as long as it has no adverse effect. Such oily components include, for example, almond oil, olive oil, tsubaki oil, persic oil, peppermint oil, soybean oil, sesame oil, mink oil, cotton seed oil, corn oil, safflower oil, palm oil, eucalyptus oil, castor oil, hydrogenated castor oil, soybean lecithin, squalene, dl- or 1-menthol, 1-menthone, 1-menthone, limonene, pinene, piperitone, terpinene, terpinolene, terpinol, carbeol, dl-camphor, N-methyl-2-pyrrolidone, or liquid paraffin. This component is preferably peppermint or eucalyptus oil. One or more types of such oily components may be used in combination. Its content is preferably between 0.5% by weight (more preferably 1% by weight) and 10% by weight (more preferably 5% by weight) of the total weight of the formulation.

Excessive amounts of these solvents may cause separation of the oily component from the formulation obtained by kneading them with a water-soluble base and the resulting formulation may cause skin irritation. Therefore, it is preferred that the solvents are mixed together in amounts not to cause the phenomena mentioned above.

The skin permeation accelerator may be any common one without particular limitation as far as it does not exert any other influence. Preferred skin permeation accelerators include, for example, alcohols and polyhydric alcohols such as ethanol, propylene glycol, 1,3-butanediol, and 1,2,6-hexanetriol; fatty acids such as lactic acid, oleic acid, linolic acid, and myristic acid, and their esters; and animal oil, vegetable oil, and a terpene compound such as peppermint oil, 1-menthol, dl-camphor, and N-methyl-2-pyrrolidone. These skin permeation accelerators can be also used as solvents or as the moisturizers described later.

The water-soluble polymer that can be used as an adhesive agent and/or film-former may be any common compound without particular limitation as far as it does not exert any other influence. Such water-soluble polymers include, for example, polyacrylic acid; sodium polyacrylate; an acrylic ester copolymers and their emulsions; cellulose derivatives such as methylcellulose, ethylcellulose, carboxymethylcellulose, and sodium carboxymethylcellulose; gum arabic; gelatin; casein; polyvinyl alcohol; polyvinylpyrrolidone; methyl vinyl ether/maleic acid anhydride copolymer and its emulsion; and natural polysaccharide such as agar. One or more types of these compounds may be used in combination and their content is preferably between 3% by weight (more preferably 5% by weight) and 30% by weight (more preferably 20% by weight) of the total weight of the formulation.

If a water-soluble polymer such as polyacrylic acid or sodium polyacrylate is used, activated alumina, synthetic aluminum silicate, or aluminum hydroxide can be used as an aluminum compound that can exhibit a cross-linking reaction.

In addition, acryl starch; polyhydric alcohol such as glycerol, propylene glycol, polyethylene glycol, or D-sorbitol is preferably used as a moisturizer, and one or more such compounds may be used in combination. Their content is preferably between 5% by weight (more preferably 10% by weight) and 60% by weight (more preferably 45% by weight) of the total weight of the formulation.

The oil-soluble polymer that can be used as an adhesive agent and/or a tackifier may be any common one without particular limitation as far as it does not exert any other influence. Such oil-soluble polymers include natural rubber, isoprene rubber, polyisobutylene rubber, styrene-butadiene rubber, a styrene-isoprene-styrene block copolymer, a styrene-butadiene-styrene block copolymer, a (meth) acrylic ester copolymer, silicone resin, rosin, polybutene, lanoline, vaseline, plastibase, beeswax, and solid paraffin. One or more such compounds may be used in combination, and their content is preferably between 5% by weight (more preferably 10% by weight) and 95% by weight (more preferably 80% by weight) of the total weight of the formulation.

Moreover, the desired amount of surfactant such as sorbitan monooleate or polyoxyethylene sorbitan monooleate; a pH regulator such as tartaric acid or citric acid; or other pharmaceutically acceptable additives such as bentonite, kaolin, talc, or titanium white can be used. Its content is preferably between 0.1% by weight (more preferably 0.5% by weight) and 15% by weight (more preferably 10% by weight) of the total weight of the formulation.

An external formulation according to this invention is preferably:

(1) an anti-inflammatory analgesic external formulation containing, at least 0.1 to 5% by weight of Loxoprofen sodium, 0.5 to 5% by weight of crotamiton, 0.5 to 80% by weight of a solvent and/or a skin permeation accelerator, 3 to 30% by weight of water-soluble polymer and/or 5 to 95% by weight of oil-soluble polymer, and 5 to 60% by weight of moisturizer, all of the total weight of the formulation.

It is more preferably:

(2) an anti-inflammatory analgesic external formulation containing, at least 0.15 to 2% by weight of Loxoprofen sodium, 1 to 2% by weight of crotamiton, 0.5 to 80% by weight of a solvent and/or a skin permeation accelerator, 5 to 20% by weight of a water-soluble polymer and/or 10 to 80% by weight of an oil-soluble polymer, and 10 to 45% by weight of a moisturizer, all based on the total weight of the formulation.

It is more preferably:

(3) an anti-inflammatory analgesic external formulation containing, at least 0.5 to 2% by weight of Loxoprofen sodium, 1 to 2% by weight of crotamiton, 0.5 to 80% by weight of a solvent and/or a skin permeation accelerator, 5 to 20% by weight of a water-soluble polymer and/or 10 to 80% by weight of an oil-soluble polymer, and 10 to 45% by weight of a moisturizer, all of the total weight of the formulation.

The present anti-inflammatory analgesic external formulation can generally be manufactured using the following preparation method.

When an external formulation containing Loxoprofen as an active ingredient is prepared, the present external formulation can be obtained by dissolving Loxoprofen in crotamiton and optionally adding thereto any of the above "various bases used for common external formulations".

On the other hand, when an external formulation containing a pharmaceutically acceptable salt of Loxoprofen as an active ingredient is prepared, an external formulation can be obtained by dissolving a pharmaceutically acceptable salt of Loxoprofen in an appropriate solvent (for example, water, methanol, ethanol or the like), mixing this solution with crotamiton, and optionally adding thereto any of the above "various bases used for common external formulations". Any of the above "various bases used for common external formulations" can be added to the solution of the active ingredient mentioned above or crotamiton before mixing the solution with crotamiton.

In particular, when an external formulation containing Loxoprofen sodium as an active ingredient is prepared, this external formulation can be specifically manufactured as follows.

The mixture containing Loxoprofen sodium is prepared by dissolving 0.1 to 5% by weight of Loxoprofen sodium in 20 to 60% by weight of a solvent (for example, water), adding the solution to a mixture of 5 to 20% by weight of sodium polyacrylate, 20 to 35% by weight of glycerol, 1 to 5% by weight of alcohols, and an appropriate amount of a pH regulator solution that has been prepared in advance, and stirring the mixture. On the other hand, a mixture containing crotamiton is prepared by mixing 0.5 to 5% by weight of crotamiton, 0.5 to 10% by weight of a solvent and/or a skin permeation accelerator, and an appropriate amount of pharmaceutically acceptable additive. Then, the desired external formulation is prepared by adding the mixture containing crotamiton to the mixture containing Loxoprofen sodium whilst stirring, adding thereto an appropriate amount of an aqueous suspension of a cross-linking reagent (for example, aluminum hydroxide gel or the like), and sufficiently kneading the mixture.

A formulation with a smaller amount of water content can be manufactured by adding 10 to 30% by weight of an oil-soluble polymeric compound to the above external formulation.

When an external formulation mainly containing oil-soluble polymers is prepared, an oily formulation can be manufactured by using isoprene or polyisobutylene as an adhesive agent, in the case of solvent method, or a styrene-isobutylene block copolymer as an adhesive agent, in the case of hot-melt method, and using a tackifier as well as crotamiton and the above oily component as a solvent and skin permeation accelerator.

According to this invention, the external formulation containing Loxoprofen sodium prepared in this manner is spread over an appropriate support, for example, a non-woven fabric or flannel, and a peel-off film made of polyethylene, polypropylene, polyester or the like is applied to the exposed surface of the formulation that is opposite to the surface thereof facing the support. The resulting formulation can be used as a patch.

In addition, without spreading the formulation on the support, the present external formulation can be used as an ointment or cream that is applied to the affected part as it is.

It can also be used as a lotion by diluting it with an aqueous solvent (for example, water, ethanol or the like), and optionally adding thereto a suspending agent (for example, gum arabic, sodium alginate, sodium carmellose, or hydroxypropylcellulose) or an emulsifing agent (for example, sorbitan monooleate or polyoxyethylene sorbitan monooleate) to homogenize the entire solution.

Alternatively, it can be used as an aerosol by diluting it with a solvent to reduce viscosity, adding thereto a suspending agent or an emulsifing agent, and filling the solution in an appropriate container together with a propellant (for example, dimethyl ether or liquefied natural gas).

The dosage of the anti-inflammatory analgesic external formulation of this invention may depend on the symptom, age of the patient, and the amount of active ingredients in the formulation, but it is desirable that an external formulation corresponding to 0.005 g (preferably 0.01 g and more preferably 0.05 g) to 100 g (preferably 50 g and more preferably 10 g) per day of Loxoprofen is applied to the affected part of the adult. Due to its persistency, the present external formulation is expected to provide a sufficient anti-inflammatory analgesic effect when applied once a day, but the daily dosage of an external formulation may be applied to the affected part dividedly in several times.

The anti-inflammatory analgesic external formulation of this invention is effective on the prevention or treatment of osteoarthritis, rheumatoid arthritis, lumbago, scapulo-humeral periarthritis, tendovaginitis, inflammation of tendon peripheries, humeral epicondylitis (tennis elbow), muscle pain, or swelling/pain after trauma.

BEST MODE FOR CARRYING OUT THE INVENTION

This invention is described below with reference to examples, comparative examples, and test examples. However, the invention is not limited to these examples.

EXAMPLE 1

External formulation containing 2% of Loxoprofen sodium 2.268 g of Loxoprofen sodium dihydrate (equivalent to 2 g of Loxoprofen sodium was added to 8 ml of water and dissolved therein. Then, 0.6 g of tartaric acid was dissolved in 45.5 ml of water; 11.5 g of sodium polyacrylate and 27 g of glycerol were added to the solution and mixed together, and the aqueous solution of Loxoprofen sodium prepared above was added to the mixture, was followed by sufficient kneading to prepare a mixture containing Loxoprofen sodium (mixture A) . Next, 2 g of crotamiton, 1 g of peppermint oil, and 2.5 g of kaolin were mixed to prepare a mixture containing crotamiton (mixture B) . Mixture B was added to mixture A whilst stirring, and 1 ml of aqueous dispersion containing 0.05 g of aluminum hydroxide gel was added to the mixture and the resulting mixture was mixed together. The weight of the mixture obtained was measured, then, water was added until the weight became 100 g, and the mixture was sufficiently kneaded. The resulting external formulation containing 2% of Loxoprofen sodium was spread over a nonwoven fabric so as to occupy in an amount of 10 g/10×14 cm, and a polyethylene film was put on the formulation and the resulting formulation was cut into pieces of a certain desired size for use as a test sample.

EXAMPLE 2

External formulation containing 1.2% of Loxoprofen sodium 1.361 g of Loxoprofen sodium dihydrate (equivalent to 1.2 g of Loxoprofen sodium) was dissolved in 4 ml of water.

Then, the solution was treated in the same manner as described in Example 1 to obtain an external formulation containing 1.2% of Loxoprofen sodium as a test sample.

EXAMPLE 3

External formulation containing 1% of Loxoprofen sodium 1.134 g of Loxoprofen sodium dihydrate (equivalent to 1 g of Loxoprofen sodium) was dissolved in 4 ml of water.

Then, the solution was treated in the same manner as described in Example 1 to obtain an external formulation containing 1% of Loxoprofen sodium as a test sample.

EXAMPLE 4

External formulation containing 0.6% of Loxoprofen sodium 0.68 g of Loxoprofen sodium dihydrate (equivalent to 0.6 g of Loxoprofen sodium) was dissolved in 4 ml of water.

Then, the solution was treated in the same manner as described in Example 1 to obtain an external formulation containing 0.6% of Loxoprofen sodium as a test sample.

EXAMPLE 5

External formulation containing 0.5% of Loxoprofen sodium 0.567 g of Loxoprofen sodium dihydrate (equivalent to 0.5 g of Loxoprofen sodium) was dissolved in 4 ml of water.

Then, the solution was treated in the same manner as described in Example 1 to obtain an external formulation containing 0.5% of Loxoprofen sodium as a test sample.

EXAMPLE 6

External formulation containing 0.3% of Loxoprofen sodium 0.34 g of Loxoprofen sodium dihydrate (equivalent to 0.3 g of Loxoprofen sodium) was dissolved in 4 ml of water.

Then, the solution was treated in the same manner as described in Example 1 to obtain an external formulation containing 0.3% of Loxoprofen sodium as a test agent.

EXAMPLE 7

External formulation containing 0.25% of Loxoprofen sodium 0.284 g of Loxoprofen sodium dihydrate (equivalent to 0.25 g of Loxoprofen sodium) was dissolved in 4 ml of water.

Then, the solution was treated in the same manner as described in Example 1 to obtain an external formulation containing 0.25% of Loxoprofen sodium as a test agent.

EXAMPLE 8

External formulation containing 0.15% of Loxoprofen sodium 0.17 g of Loxoprofen sodium dihydrate (equivalent to 0.15 g of Loxoprofen sodium) was dissolved in 4 ml of water.

Then, the solution was treated in the same manner as described in Example 1 to obtain an external formulation containing 0.15% of Loxoprofen sodium as a test agent.

EXAMPLE 9

External formulation containing 1% of Loxoprofen sodium

In Example 2, similar process were carried out but using of 1 g, instead of 2g, of crotamiton to obtain an external formulation containing 1% of Loxoprofen sodium as a test sample.

EXAMPLE 10

Lotion containing 1% of Loxoprofen sodium 1.134 g of Loxoprofen sodium dihydrate (equivalent to 1 g of Loxoprofen sodium) was dissolved in 66.8 ml of water.

1 g of crotamiton and 0.25 g of peppermint oil were added to the mixture of 0.2 g of sodium carboxymethylcellulose in 10 g of glycerol and 20 g of propylene glycol and sufficiently mixed together. The solution of Loxoprofen mentioned above was added to this mixture, and 0.5 g of Tween 80 and 0.25 g of Span 20 as surfactants were then added to the mixture whilst stirring to prepare a lotion containing 1% of Loxoprofen sodium.

EXAMPLE 11

External formulation containing 1% Loxoprofen 11.5 g of sodium polyacrylate and 27 g of glycerol were added to the solution of 0.6 g of tartaric acid in 45.5 ml of water, and mixed together to prepare a mixture containing glycerol. Then, 2.5 g of kaolin was added to the solution of 1 g of Loxoprofen in a mixture of 2 g of crotamiton and 1 g of peppermint oil, then, the resulting mixture was sufficiently kneaded to prepare a mixture containing Loxoprofen. The mixture containing Loxoprofen was added to the mixture containing glycerol whilst stirring, and 1 ml of aqueous dispersion containing 0.05 g of aluminum hydroxide gel was added to the mixture and mixed together. The weight of the mixture obtained was measured, and water was added thereto until the weight reached 100 g. The mixture was then sufficiently kneaded to prepare an external formulation containing 1% Loxoprofen.

Reference Example 1

External formulation containing a 1% of trans-OH form 11. 5% of sodium polyacrylate and 27 g of glycerol were added to the solution of 0.6 g of tartaric acid in 45.5 ml of water, and mixed together to prepare a mixture containing glycerol. Then, 2.5 g of kaolin was added to the solution of 1 g of trans-OH form, which is an active metabolite, in a mixture of 2 g of crotamiton and 1 g of peppermint oil, and the resulting mixture was then sufficiently kneaded to prepare a mixture containing a trans-OH form. The mixture containing a trans-OH form was added to the mixture containing glycerol whilst stirring and 1 ml of aqueous dispersion containing 0.05 g of aluminum hydroxide gel was added to the mixture and mixed together. The weight of the mixture obtained was measured, and water was added thereto until the total weight reached 100 g. The mixture was then sufficiently kneaded. The resulting external formulation containing 1% of trans-OH form was spread over a non-woven fabric so as to occupy in an amount of 10 g/10×14 cm, and a polyethylene film was put on the formulation and the formulation was cut into pieces of a certain desired size for use as a test sample.

Comparative Example 1

In Example 3, similar processes were carried out except that crotamiton was not used to obtain the external formulation containing 1% Loxoprofen sodium as a test sample.

Comparative Example 2

In Example 3, similar processes were carried out but using 2 g of oleic acid instead of 2 g of crotamiton to obtain an external formulation containing 1% Loxoprofen sodium as a test sample.

Comparative Example 3

In Example 3, similar processes were carried out but using 2 g of isopropyl myristate instead of 2 g of crotamiton to obtain an external formulation containing 1% Loxoprofen sodium as a test sample.

Test Example 1

Deposition of crystals in the external formulation containing Loxoprofen sodium with the passage of time Immediately after manufacturing, with regard to the external patches obtained in Examples 1 and 9 and Comparative Examples 1 to 3, the deposition of crystals of Loxoprofen sodium was observed with naked eye or under a microscope in the formulation. Then, samples were stored in an alminum pouch at room temperature, and the deposition of crystals was observed with passage of time in the same manner as described above.

The results are shown in Table 1.

TABLE 1

Deposition of crystals in the external formulation containing loxoprofen sodium with passage of time

| Formulation | Number of days from the manufacturing date until crystals were deposited |
|---|---|
| Formulation as described in Comparative Example 1 | No deposition for 2 years |
| Formulation as described in Reference Example 1 | No deposition for 2 years |
| Formulation as described in Comparative Example 1 | 12 days |
| Formulation as described in Comparative Example 2 | 4 months |
| Formulation as described in Comparative Example 3 | 4 days |

As shown clearly in Table 1, no Loxoprofen was deposited over a long period of time in the formulations as described in Examples 1 and 9 which contain crotamiton as a solvent. That is, the addition of crotamiton significantly improved the stability of the external formulations containing Loxoprofen sodium.

Test Example 2

Permeability tests for in vitro skin of external formulations containing Loxoprofen sodium The external patches obtained as described in Example 3, Comparative Example 1, and Reference Example 1 were subjected to permeability tests for in vitro using rat skin. The concentrations of Loxoprofen, per se, and of the trans-OH form, which is an active metabolite, were measured to examine their skin permeability after application.

Each of external patches of 1 cm in diameter was used for tests.

Sodium pentobarbital was intraperitoneally administered in a content of 1 mg/kg to Wistar Imamichi male rats (7 weeks of age), which were then put under anesthesia. After that, a hair clipper and a shaver were used to shave hair on the abdomen. Then, the skin was picked out therefrom in the form of a disk of 2.2 cm in diameter. The fat layer under the dermal tissue of the skin picked out was removed, and the resulting skin was fixed to a vertical diffusion cell for permeability tests, which had been maintained beforehand at 37° C. The formulation was applied to the stratum corneum epidermidis on the diffusion cell, and 4.5 ml of Tyrode's solution was added to the dermal layer side as a receiver solution. During a 24-hour patch test, 0.5 ml of receiver solution was occasionally sampled as appropriate and was subjected to HPLC to measure the concentration of the drug. When the receiver liquid was sampled, 0.5 ml of Tyrode's solution without drug, being kept warm at 37° C., was added to maintain the volume of the receiver liquid constant. The cumulative amount of the drug after skin permeation increased linearly with the passage of time.

The HPLC measurement method is shown below.

An equal amount of ethanol solution [10 mg/ml of ethyl p-hydroxybenzoate (produced by Wako Pure Chemical Industry Co., Ltd.)] as an internal standard was added to the samples taken out and admixed together. The mixture was centrifuged at 12,000 rpm for 5 minutes, and the supernatants were used as samples for HPLC.

HPLC measuring conditions

Column: CAPCELLPACK C18 (4.6×150 mm; produced by Shiseido Co., Ltd.)

Mobile phase: 1% phosphoric acid/acetonitrile=$\frac{5}{2}$

Column temperature: 40° C.

Flow rate: 1 ml/min.

Detected wavelength: 222 nm

Retention time: Loxoprofen: 12.7 minutes trans-OH form: 10.7 minutes cis-OH form: 11.9 minutes ethyl p-benzoate: 7.6 minutes The results are shown in Table 2.

TABLE 2

Permeability tests for in vitro skin of external formulations containing loxoprofen sodium

| Formulation | Skin permeation flux (nmol/cm$^2$/hr) | |
| --- | --- | --- |
| | Loxoprofen | Trans-OH form |
| Formulation as described in Example 3 | 2.50 | 1.25 |
| Formulation as described in Comparative Example 1 | 1.25 | 0.35 |
| Formulation as described in Reference Example 1 | — | 0.50 |

The results of the tests using formulations as described in Example 3 and Comparative Example 1 clearly indicate that Loxoprofen sodium is surprisingly converted into a trans-OH form, which is it's active metabolite, in the skin without passing through the liver or kidney. In addition, when the formulations as described in Example 3 and Comparative Example 1 are compared together, the addition of crotamiton served to double the permeation rate of Loxoprofen and quadruple the increasing rate of the trans-OH form in the receiver liquid (this can be considered to correspond to the trans-OH form which would exist under the dermal layer). As a result, a very large amount of trans-OH form was present in the receiver solution in a certain time after the application of the formulation.

In addition, the results of the formulation as described in Reference Example 1 indicate that the trans-OH form, which is an active metabolite, showed low permeability through the skin and that the increasing rate of the trans-OH form in the receiver solution was small even when the trans-OH form per se was administered. When these results are compared with the results of the formulation as described in Example 3, it is found unexpectedly that when Loxoprofen sodium, which is a prodrug, was administered; the increasing rate of the trans-OH form in the receiver liquid was higher, resulting in a larger amount of trans-OH form in the receiver liquid.

Test Example 3

Concentration in tissues of metabolites after the application of external formulations containing Loxoprofen sodium to skin.

Patches produced according to the method as described in Example 3, labeled with $^{14}$C and containing 1% of Loxoprofen sodium, were applied to the skin on the back of rats for 4, 8, and 24 hours, concentrations of active metabolites in the dermal tissue of the skin and in blood plasma were measured.

Body hair on the back of Wistar Imamichi male rats (7 to 8 weeks of age; three rats in each group) was removed using a hair clipper and a shaver, and formulation pieces in a size of 2×1.75 cm were applied on the skins of the rats. The blood plasma (0.5 to 2 ml) was sampled at each different times from the rats to which the formulation was applied and the rats were then sacrificed. By stripping sufficiently by use of a cellophane adhesive tape, the stratum corneum was removed from the skin in the middle of the site to which the formulation was applied. A punch ($\phi$1.0 cm) was used to punch the dermal portion out to remove it. The removed portion was hashed after fat and capillaries were removed from the dermal portion. Then, a quintuple amount of methanol was added to the hashed skin slices to homogenize it, and the resulting mixture was centrifuged at 1,800×g and 4° C. for 10 minutes to obtain the supernatant as an extract. The blood plasma mentioned above was similarly treated on to obtain an extract. After each extract was dried and solidified under reduced pressure at room temperature, it was redissolved in a small amount of methanol and was subjected to thin layer chromatography (TLC) to measure the concentration of active metabolites.

Measurements based on the TLC method were executed as follows.

The sample in methanol mentioned above was applied in lines to a TLC plate (silica gel 60F254; Art NQ. 5714, manufactured by MERCK Co.) together with the authentic sample of Loxoprofen per se and its metabolite, and a solution of benzene:acetone:acetic acid (80:15:5) was used as a developing solvent to develop the sample three times so that the length of the developing solvent reached 15 cm. After development, the TLC plate was dried and covered with a protective film (4 $\mu$m; manufactured by DIAFOIL Co.), and was then adhered to an imaging plate (TYPE-BA; manufactured by Fuji Film Co., Ltd.) and exposed in a lead sealed box for 24 hours. After exposure, a bio-image analyzer (FUJIX BA100; manufactured by FUJI Film Co., Ltd.) was used to read a radio-active image on imaging plate to create an autoradiogram. The developed position of the authentic sample of the metabolite was confirmed using a 254-nm ultraviolet lamp. Then, the autoradiogram was fractionated into a background section and a radio-active band region of Loxoprofen (an unchanged form) or trans-OH form (an active metabolite) to calculate from each emission intensity the ratios of Loxoprofen (an unchanged form) and trans-OH form (an active metabolite).

The concentrations of Loxoprofen (an unchanged form) and trans-OH form (an active metabolite) were calculated in the following manner.

The concentrations were determined using the total concentration calculated from the radio-active concentration of the sample prior to the TLC operation as well as the ratios calculated above.

The results are shown in Table 3.

TABLE 3

Concentration of Loxoprofen metabolites in the tissues

| Tissue | Time | Loxoprofen | ($\mu$g/g or $\mu$g/ml) Trans-OH form |
|---|---|---|---|
| Dermel layer | 4 hours | 61.04 | 4.17 |
| ($\mu$g/g) | 8 hours | 60.16 | 4.00 |
|  | 24 hours | 60.48 | 3.73 |
| Blood plasma | 4 hours | 0.20 | 0.11 |
| ($\mu$g/ml) | 8 hours | 0.28 | 0.17 |
|  | 24 hours | 0.13 | 0.12 |

As shown clearly in Table 3, the concentration of trans-OH form, which is an active metabolite, in the dermal layer was 40 times higher than that in the blood plasma, and the concentration of Loxoprofen, which is an unchanged form, in the dermal layer was 300 times higher than that in the blood plasma. This indicates that Loxoprofen sodium transferred directly to the topical site.

Furthermore, since its amount remained constant during administration, this indicates that this formulation provides sufficient efficacy when applied once a day.

Test Example 4

Suppression of carrageenin crural edema

The external patches of Loxoprofen sodium as described in Examples 2, 4, 6, and 8 were investigated for carrageenin crural edema suppression effect.

SD male rats (5 weeks of age) were used for the tests, with 8 rats constituting each group. The hair on the left posterior feet of the rats was shaven using an electric hair clipper, and 0.1 ml of 0.5% saline solution of carrageenin was injected under the foot sole skin of the left posterior foot to induce inflammation. Immediately after inflammation was induced, formulation in a size of 2×1.75 cm were applied to the feet, and the volume of the foot sole was measured at 1, 2, 3, 4, and 5 hours after the induction to observe the inflammation suppression effect of the present external formulation using as an edema rate the increasing rate in the volume of the foot sole after the induction of inflammation relative to the same volume prior to the injection of the inflammation inducing agent. The suppression effect reached its maximum value at 4 hours after the induction.

For comparison, a "control group" was provided in which inflammation was induced as described above and in which rats were then left untreated.

Furthermore, a "base group" was provided in which rats were treated using a formulation of the same composition as described in Example 1 except for the absence of Loxoprofen sodium. The results are shown in Table 4.

TABLE 4

Rat carrageenin edema suppression effect (4 hours after induction)

| Formulation | Edema rate (%) (average ± standard error) | Suppression rate (%) |
|---|---|---|
| Control group | 65.2 ± 4.7 |  |
| Base group | 58.6 ± 4.7 | 10.2 |
| Formulation as described in Example 2 | 31.2 ± 3.1** | 52.1 |
| Formulation as described in Example 4 | 33.3 ± 3.1** | 48.9 |
| Formulation as described in Example 6 | 36.9 ± 3.0* | 43.4 |
| Formulation as described in Example 8 | 38.3 ± 4.4* | 41.2 |

Significant difference from the base group
*: $p < 0.01$, **: $p < 0.001$

As shown clearly in Table 4, the formulation containing 0.15% or more of Loxoprofen sodium was observed to exhibit a significant suppression effect against the control and base groups depending on the concentration. Thus, it is evident that this formulation is effective on acute inflammation.

Test Example 5

Anti-inflammatory effect on adjuvant arthritis

The patches containing Loxoprofen sodium as described in Examples 1, 3, 5, and 7 were investigated for anti-inflammatory effect on adjuvant arthritis.

Lewis male rats (8 weeks of age) were used for the tests, with 10 rats constituting one group. *Mycobacterium butyricum* that had been killed by heating were refined, and the refined cells were then suspended in liquid paraffin until the volume of the suspension reached 6 mg/ml. The suspension was then sterilized at 120° C. and used as an adjuvant. The volume of both posterior feet was measured, and 0.1 ml of the killed cell suspension, which had been heated up to 50° to 60° C., was injected into the tail base skin. An adjuvant was administered to the rats for which inflammation had been induced, and 19 days later, formulation pieces 2×1.75 cm in size into which the formulation had been cut were each applied to the periphery of the sole of the right posterior feet. The formulation was allowed to remain application for 9 consecutive days. The increase in the volume of the soles of both posterior feet on the day when application was started was defined as a 100% edema rate, and changes in this volume were observed every day.

The "control group" and "base group" were the same as described in [Test Example 4].

The results are shown in Table 5.

TABLE 5

Anti-inflammatory effect on the adjuvant arthritis

Edema rate(%) (average ± standard error) The number enclosed in parentheses indicates the edema suppression rate(%)

| Formulation | 21 days | 26 days | 31 days |
|---|---|---|---|
| Control group | 93.1 ± 4.77 | 86.7 ± 5.57 | 79.6 ± 3.98 |
| Base group | 81.4 ± 4.70 (12.6) | 73.1 ± 3.89 (15.7) | 65.4 ± 3.89 (17.9) |
| Formulation as described in Example 1 | 74.4 ± 4.00 (20.1) | 52.3 ± 2.38* (39.6) | 48.0 ± 3.20* (39.8) |

TABLE 5-continued

Anti-inflammatory effect on the adjuvant arthritis

Edema rate(%)
(average ± standard error)
The number enclosed in parentheses indicates
the edema suppression rate(%)

| Formulation | 21 days | 26 days | 31 days |
|---|---|---|---|
| Formulation as described in Example 3 | 69.1 ± 4.77 (25.8) | 51.6 ± 2.38* (40.5) | 46.4 ± 2.36* (41.7) |
| Formulation as described in Example 5 | 76.6 ± 3.99 (17.7) | 59.0 ± 2.38* (32.2) | 50.2 ± 2.39* (36.9) |
| Formulation as described in Example 7 | 75.2 ± 5.43 (19.2) | 61.3 ± 3.10 (29.3) | 59.3 ± 3.85 (25.6) |

Significant difference from the base group
*: $p < 0.01$

As shown clearly in Table 5, the formulation containing 0.5% or more of Loxoprofen sodium was confirmed to provide a significant suppression effect against the control and base groups depending on the concentration. Thus, this formulation is clearly effective on chronic inflammation.

Industrial Applicability

By addition of crotamiton as a solvent to an external formulation containing Loxoprofen or its pharmaceutically acceptable salt, Loxoprofen is prevented from being deposited in crystal form, and it is thus possible to provide a formulation whose active ingredients are distributed appropriately. This formulation enables a substantial increase in the rate and amount of transcutaneous absorption of Loxoprofen, and also enables the sustained supply of Loxoprofen, to allow a sufficient concentration of Loxoprofen to be continuously accumulated in the skin at the applied site. Then, Loxoprofen is transformed into the trans-OH form in the skin, thus enabling a sufficient amount of trans-OH form to be provided at the applied site. As a result, the application of this formulation can provide an excellent topical analgesic effects. The anti-inflammatory analgesic external formulation of this invention shows less irritation on the skin and is effective in the prevention or treatment of, for example, osteoarthritis, rheumatoid arthritis, lumbago, scapulohumeral periarthritis, tendovaginitis, inflammation of tendon peripheries, humeral epicondylitis (tennis elbow), muscle pain, or swelling or pain after trauma.

What is claimed is:

1. An anti-inflammatory analgesic patch comprising Loxoprofen or its pharmaceutically acceptable salt, crotamiton, a solvent comprising water and a skin permeation accelerator, a water-soluble polymer and a moisturizer as external formulation components, wherein the patch contains an effective amount of Loxoprofen or its pharmaceutically acceptable salt in such a manner that it is metabolized into a trans-OH form in the skin when applied to the skin so as to make a concentration of the trans-OH form higher in a dermal layer of the skin at an applied site than in blood plasma.

2. An anti-inflammatory analgesic patch according to claim 1, comprising 0.5–2.0 wt % of Loxoprofen sodium, 1–2 wt % of crotamiton, 0.5–80 wt % of the solvent and the skin permeation accelerator, 5–20 wt % of the water-soluble polymer and 10–45 wt % of the moisturizer, wherein said patch contains 20–80 wt % of water as said solvent, based on the total weight of said external formulation.

3. An anti-inflammatory analgesic patch according to claim 2, wherein the patch consists of the external formulation, a support and a peel-off film, wherein the external formulation is spread over the support and the peel-off fiim is applied onto the external formulation on a surface opposite to the support.

* * * * *